United States Patent
Liang et al.

(10) Patent No.: US 12,135,310 B2
(45) Date of Patent: Nov. 5, 2024

(54) REFERENCE VALUE QUANTIFICATION METHOD FOR MODIFIER DOSAGE OF MODIFIED ASPHALT

(71) Applicants: Changsha University of Science and Technology, Hunan (CN); Central South University, Hunan (CN)

(72) Inventors: Bo Liang, Hunan (CN); Zhengchun Liu, Hunan (CN); Jianlong Zheng, Hunan (CN)

(73) Assignees: Changsha University of Science and Technology, Changsha (CN); Central South University, Changsha (CN)

( * ) Notice: Subject to any disclaimer, the term of this patent is extended or adjusted under 35 U.S.C. 154(b) by 763 days.

(21) Appl. No.: 17/413,629

(22) PCT Filed: Aug. 16, 2019

(86) PCT No.: PCT/CN2019/101149
§ 371 (c)(1),
(2) Date: Dec. 3, 2021

(87) PCT Pub. No.: WO2020/119166
PCT Pub. Date: Jun. 18, 2020

(65) Prior Publication Data
US 2022/0341873 A1  Oct. 27, 2022

(30) Foreign Application Priority Data

Dec. 13, 2018 (CN) .......................... 201811525955.3

(51) Int. Cl.
*G01N 27/49* (2006.01)
*G01N 33/42* (2006.01)
*G16C 60/00* (2019.01)

(52) U.S. Cl.
CPC ............. *G01N 27/49* (2013.01); *G01N 33/42* (2013.01); *G16C 60/00* (2019.02)

(58) Field of Classification Search
CPC .................................................... G01N 27/49
See application file for complete search history.

(56) References Cited

U.S. PATENT DOCUMENTS

2018/0057686 A1* 3/2018 Williams .................. E01C 7/18

OTHER PUBLICATIONS

CN 105136895 (English Translated) (2015).*

* cited by examiner

*Primary Examiner* — Hyun D Park
(74) *Attorney, Agent, or Firm* — Morse, Barnes-Brown & Pendleton, P.C.; Martin Z. Zhang, Esq.

(57) ABSTRACT

Disclosed is a design reference value quantification method for a modifier dosage of modified asphalt. A curve of unsaturation degree of the modified asphalt as a function of the modifier dosage is plotted, in which the unsaturation degree of a series of modified asphalts is determined by potentiometric titration; further, an inflection point of the unsaturation degree of the modified asphalt as a function of the modifier dosage in the asphalt is obtained by data fitting and analysis, and a reference value of the dosage of the modifier added in the process design of the modified asphalt is established.

6 Claims, 4 Drawing Sheets

REFERENCE VALUE QUANTIFICATION METHOD FOR MODIFIER DOSAGE OF MODIFIED ASPHALT

CROSS REFERENCE TO RELATED APPLICATION

This application is the national stage of International Application No. PCT/CN2019/101149, filed on Dec. 13, 2018, which claims the benefit and priority of Chinese Patent Application No. 201811525955.3 filed on Dec. 13, 2018, the disclosures of which are incorporated by reference herein in their entirety as part of the present application.

TECHNICAL FIELD

The present disclosure belongs to the technical field of pavement construction, and particularly to a design reference value quantification method for a modifier dosage of modified asphalt.

BACKGROUND ART

Asphalt is widely used in road construction, especially the polymer modified asphalt which can significantly improve the aging performance, durability, permanent deformation, and thermal sensitivity of the pavement. Among them, thermoplastic styrene-butadiene-styrene (SBS) block copolymer is the most widely used polymer that can comprehensively improve pavement performance. However, SBS and matrix asphalt are thermodynamically incompatible, resulting in the generally poor storage stability of SBS modified asphalt, which is mainly caused by unstable intermolecular physical crosslinking. Such physical crosslinking is mainly maintained depending on Van der Waals force, hydrogen bonding, and dispersive force. In order to improve storage stability, crosslinking with molecular sulfur is the most common method. It is generally accepted that sulfur not only forms chemically bonds between SBS chains, but also forms chemically bonds between SBS and asphalt molecules through sulfides or polysulfides.

At present, scholars have done a lot of research on the modification mechanism of SBS and SBS/sulfur modified asphalt. The addition of sulfur substantially improves the rheological properties of SBS modified asphalt. The difference in morphology between SBS/asphalt blend and SBS/asphalt/sulfur blend was observed by fluorescence microscopy. It was found that the SBS/asphalt/sulfur blend was a continuous polymer-rich phase, and the SBS/asphalt blend is a polymer-rich phase. The results show that sulfur promotes the formation of a continuous polymerization network of the SBS modified asphalt and further improves the performance of the SBS modified asphalt. The properties and microstructure of the asphalt provide qualitative evidence of crosslinking reactions. In the process of asphalt modification, the exact reaction mechanism of sulfurization of sulfur molecules is still unclear, which is not enough to guide the process design of the SBS modified asphalt. SBS is undoubtedly a better polymer modifier nowadays. The chemical reaction between SBS and matrix asphalt or sulfur in the modification process will result in a decrease in carbon-carbon double bond, this is because isolated carbon-carbon double bonds in the matrix asphalt and SBS molecule are vulnerable to attack during the reaction. Therefore, changes in double bonds will be direct evidence of chemical crosslinking. It has been shown that with the increase of SBS dosage, the dispersion state of the SBS in the asphalt changes from the spotted distribution wrapped by matrix asphalt to the sheet distribution, and finally to a continuous phase wrapping asphalt. The SBS dosage corresponding to the point at which the phase transition occurs further becomes a breaking point of the quality of the modified asphalt. However, the existing modifier dosage design is mainly adjusted and determined by satisfying the design of three conventional indexes (penetration, softening point, and low-temperature ductility), and mainly based on apparent performance tests and experience summaries. For example, the parameter of adding sulfur to different modified asphalts has been used for over 40 years. Therefore, it is extremely urgent to develop a quantitative parameter, especially a design for the modifier dosage, which is capable of revealing the mechanism of the interaction between asphalt molecule and modifier and optimizing asphalt modification process.

SUMMARY

In view of the deficiencies of the prior art, an object of the present disclosure is to provide a design reference value quantification method for a modifier dosage of modified asphalt. An inflection point of transition of the modifier from an dispersed phase to a continuous phase in the modified asphalt is quantitatively determined by potentiometric titration, and a reference value of the modifier dosage is determined by the inflection point, so that the effect of the modifier dosage on modified asphalt performance can be quantitatively determined.

The present disclosure provides a design reference value quantification method for a modifier dosage of modified asphalt, comprising steps of:
  (1) preparing a series of modified asphalt samples with different modifier dosages;
  (2) determining an unsaturation degree of each modified asphalt sample by potentiometric titration;
  (3) obtaining an inflection point of the unsaturation degree of the modified asphalt sample as a function of the modifier dosage by data fitting; and
  (4) determining a reference value of the modifier dosage by the inflection point.

In some embodiments, the modifier dosage in the modified asphalt sample may be 0-20 wt %, and the modifier dosage changes in a linear gradient.

In some embodiments, the modifier may be a polymer material containing olefinic bonds and acetylenic bonds.

In some embodiments, the modifier may be one or more selected from the group consisting of styrene-butadiene-styrene (SBS), styrene-butadiene rubber (SBR), and polyisoprene rubber.

In some embodiments, step (1) is specifically conducted as follows:
  preparing a plurality of groups of tetrahydrofuran solutions of modified asphalt samples with different modifier dosages, where each group solution comprises the modified asphalt sample in an amount of 0.5-10 g, and the tetrahydrofuran in an amount of 5-100 mL.

In some embodiments, step 2 is specifically conducted as follows:
  S1, adding 10-30 mL of a 0.01-1 M Wijs reagent to each tetrahydrofuran solution of the modified asphalt sample, and reacting at 30-50° C. for 8-24 h; adding 5-30 mL of a 10-1,000 g/L potassium iodide solution, and reacting for 1-60 min, to obtain product solutions;
  S2, titrating each product solution obtained in step S1 with a 0.1-2 M sodium thiosulfate solution, determining a titration end point by potentiometric titration, and recording a volume $V_1$ of the sodium thiosulfate solution consumed, in mL;

S3, preparing a blank tetrahydrofuran solution, and repeating steps S1 and S2 to obtain a volume $V_0$ of the sodium thiosulfate solution consumed by the titration of the blank tetrahydrofuran solution, in mL; and S4, calculating the unsaturation degree Y of the modified asphalt sample according to formula (1);

$$Y = \frac{126.9(V_0 - V_1)C}{10W} \quad (1)$$

where C refers to the concentration of sodium thiosulfate, in mol/L; 126.9 refers to the molar mass of iodine molecule, in g/mol; and W refers to the mass of the modified asphalt sample, in g.

In some embodiments, step 3 is specifically conducted as follows:
a) plotting a curve with the modifier dosage as an abscissa and the unsaturation degree of the modified asphalt sample as an ordinate;
b) fitting a straight line $L_1$ in a low-dosage region (ranging from 0 to 10%) of the modifier where the unsaturation degree shows linear growth, and fitting a straight line $L_2$ in a high-dosage region (ranging from 6 to 20%) of the modifier where the unsaturation degree is in plateau; and
c) determining an intersection point of the straight lines $L_1$ and $L_2$ as the inflection point O of the unsaturation degree as a function of the modifier dosage.

In some embodiments, in step (4), the abscissa value corresponding to the inflection point O indicates a design reference value of the modifier dosage in the modified asphalt.

The embodiments of the present disclosure have the principle as follows: the preparation of the modified asphalt is accompanied by changes of C=C and C≡C which are detected by a stoichiometric reaction with halogen. In the present disclosure, the quantitative effect of different modifier dosage on the unsaturation degree of modified asphalt sample is tracked by electrochemical potentiometric titration, so as to develop a method for detecting the inflection point of the unsaturation degree in a modified asphalt sample, providing a basis for quantitative calculation of a design reference value of the modifier dosage of a modified asphalt formulation.

Compared with the prior art, the present disclosure has the following beneficial effects:

The present disclosure provides a design reference value quantification method for a modifier dosage of a modified asphalt. A curve of the unsaturation degree of the modified asphalt as a function of the modifier dosage is plotted based on the change of the unsaturation degree of a series of modified asphalt determined by potentiometric titration; further, an inflection point of the unsaturation degree of the modified asphalt as a function of the modifier dosage in the asphalt is obtained by data fitting and analysis, thereby establishing a reference value of dosage of the modifier added in the process design of the modified asphalt. Compared with conventional design method for modifier dosage in modified asphalt, the present disclosure makes it possible to directly reflect the mechanism of chemical action between the modifier and matrix asphalt in the modified asphalt in essence by accurately determining the effect of the modifier dosage on the unsaturation degree of the modified asphalt, and makes it possible to directly track the process of transition of the modifier from an disperse phase to a continuous phase in the modified asphalt, which is of a positive significance to obtain a modified asphalt with high performance.

DETAILED DESCRIPTION OF THE EMBODIMENTS

The technical solutions in the embodiments of the present disclosure will be clearly and completely described below. Obviously, the described embodiments are only a part of, not all of, embodiments of the present disclosure. Based on the embodiments of the present disclosure, all other embodiments obtained by those skilled in the art without creative efforts should fall within the protection scope of the present disclosure.

Figure 1:
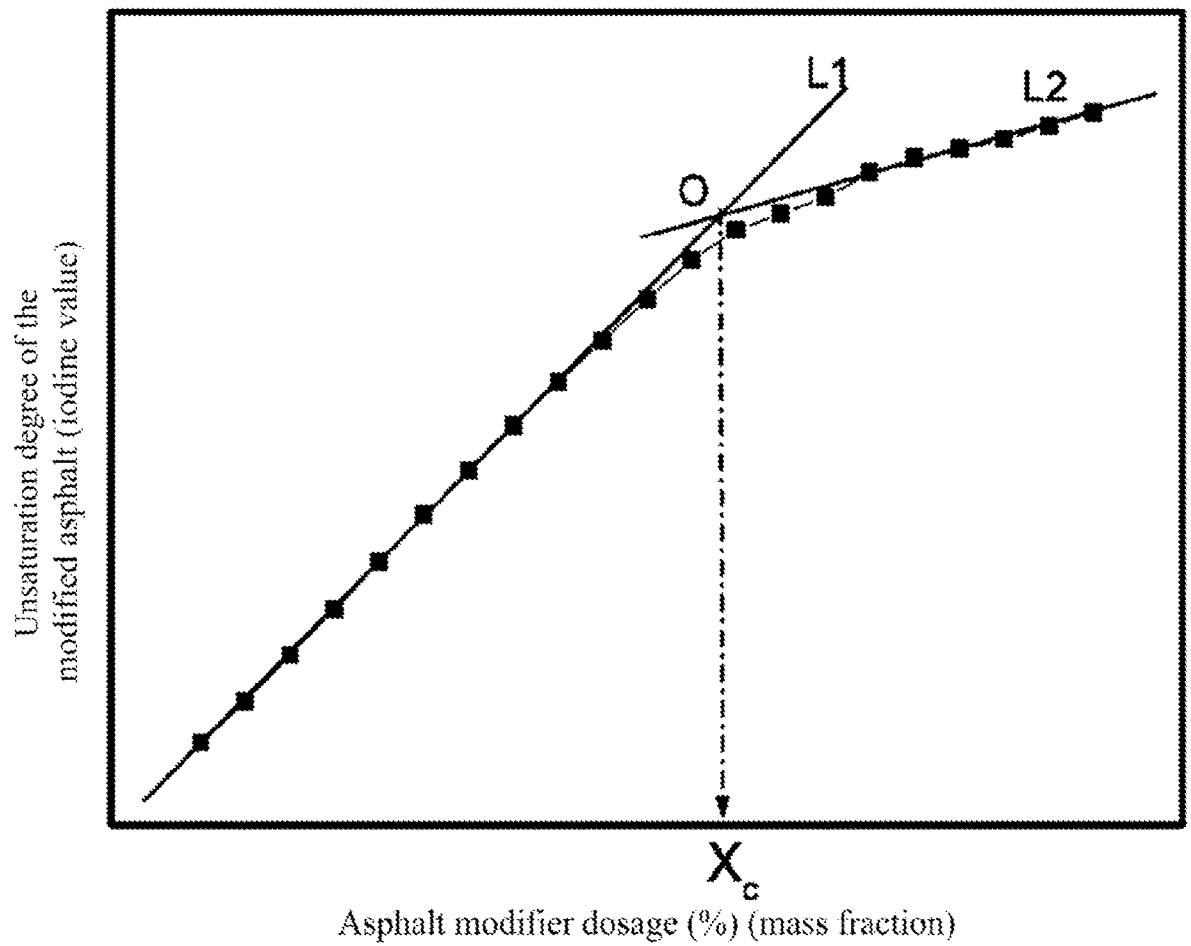
FIG. 1 shows a schematic diagram of the method for quantifying a reference value of the modifier dosage in the modified asphalt according to the examples of the present disclosure.

In some embodiments, the present disclosure provides a design reference value quantification method for a modifier dosage of modified asphalt, comprising:
step 1, preparing a plurality of groups of tetrahydrofuran solutions of modified asphalt samples with different modifier dosages, where each group solution comprises the modified asphalt sample in an amount of 0.5-10 g, and the tetrahydrofuran in an amount of 5-100 mL;
step 2, adding 10-30 mL of a 0.01-1 M Wijs reagent to each tetrahydrofuran solution of the modified asphalt sample, and reacting at 30-50° C. for 8-24 h; adding 5-30 mL of a 10-1,000 g/L potassium iodide solution, and reacting for 1-60 min, to obtain product solutions;
step 3, titrating each product solution obtained in step 2 with a 0.1-2 M sodium thiosulfate solution, determining a titration end point by potentiometric titration, and recording a volume $V_1$ of the sodium thiosulfate solution consumed, in mL;
step 4, preparing a blank tetrahydrofuran solution, and repeating steps 2 and 3 to obtain a volume $V_0$ of the sodium thiosulfate solution consumed by the titration of the blank tetrahydrofuran solution, in mL; and
step 5, calculating the unsaturation degree Y of the modified asphalt sample according to formula (1);

$$Y = \frac{126.9(V_0 - V_1)C}{10W} \quad (1)$$

where C refers to the concentration of sodium thiosulfate, in mol/L; 126.9 refers to the molar mass of iodine molecule, in g/mol; and W refers to the mass of the modified asphalt sample, in g;

step 6, plotting a curve with the modifier dosage as an abscissa and the unsaturation degree of the modified asphalt sample as an ordinate, as shown in FIG. 1; fitting a straight line $L_1$ in a low-dosage region (ranging from 0 to 10%) of the modifier where the unsaturation degree shows linear growth, and fitting a straight line $L_2$ in a high-dosage region (ranging from 6 to 20%) of the modifier where the unsaturation degree is in plateau; and step 7, determining an intersection point of the straight lines $L_1$ and $L_2$ as the inflection point O of the unsaturation degree as a function of the modifier dosage, where an abscissa value corresponding to the inflection point O indicates a design reference value of the modifier dosage in the modified asphalt.

Notably, under the condition that the process is definite, the dosage of modifier capable of producing a modifier continuous phase in asphalt is taken as a reference standard. The dosage higher than the reference standard is defined as high dosage; the dosage lower than the reference standard is defined as low dosage. Different asphalts or modifiers correspond to different reference standards.

The low-dosage region of the modifier (ranging from 0 to 10%) refers to a region of the modifier that satisfies two conditions: one is that the modifier dosage corresponds to a low dosage, i.e., lower than the above reference standard, and the other is that the modifier dosage needs to fall within the range of 0 to 10%.

The high-dosage region of the modifier (ranging from 6 to 20%) refers to a region of the modifier that satisfies two conditions: one is that the modifier dosage corresponds to a high dosage, i.e., higher than the above reference standard, and the other is that the modifier dosage needs to fall within the range of 6 to 20%.

Notably, the potentiometric titration refers to a method for determining a titration end point by measuring electric potential variation during titration; specifically, the potentiometric titration is to indicate a titration end point depending on an electrode potential jump, and before and after the titration reaches the end point, the concentration of ions to be measured in dropping liquid tends to change by an order of magnitude, leading to a potential jump; analyte content is still calculated according to the amount of titrant consumed. Therefore, in the present disclosure, the unsaturation degree of each modified asphalt sample determined by the potentiometric titration is relatively accurate. The potentiometric titration does not need to measure an electrode potential value accurately, but takes into account the potential jump. Therefore, the influence of temperature and liquid junction potential on the titration end point may be ignored. Thus, the method according to the present disclosure has an excellent anti-interference ability. Furthermore, the asphalt is black, resulting in that the titration end point can not be determined by color. Thus, the potentiometric titration in the present disclosure is not influenced by color changes.

The modifier dosage in the modified asphalt sample is 0-20 wt %, and the modifier dosage changes in a linear gradient.

The modifier is a polymer material containing olefinic bonds (C=C double bond) or acetylene bonds (C≡C triple bond); the modifier is one or more selected from the group consisting of SBS, SBR (Styrene Butadiene Rubber), and polyisoprene rubber.

The present disclosure will be further described below with reference to specific examples and drawings.

Notably, in the examples of the present disclosure, M is in mol/L (mole per liter).

Example 1

70# Matrix asphalt 1 provided by a well-known enterprise was used. According to the preparation process in the present disclosure, a certain amount of matrix asphalt and 1 g of furfural extract oil were weighed and heated to 175-180° C. SBS modifier was then added at a shear rate of 500 r/min at 175-180° C., and the resulting mixture was sheared at a shear rate of 3,000 r/min for 30 min to obtain a sample. The sample was transferred to a stirrer, and stirred at 500 r/min for 4 h, and then 0.1 g of sulfur powder as a stabilizer was added and stirred for 3 h for modification to obtain a modified asphalt. The method for preparing the modified asphalt was conducted by changing a single variable, i.e. all the modified asphalt samples were prepared with only difference in SBS modifier dosage. The formulation thereof is shown in Table 1.

TABLE 1

The formulation of the modified asphalt in Example 1

| No. | SK70# asphalt (g) | Furfural extract oil (g) | Sulfur powder (g) | SBS modifier (g) | SBS dosage (%) |
|---|---|---|---|---|---|
| 1 | 98.9000 | 1.0000 | 0.1000 | 0 | 0 |
| 2 | 98.4000 | 1.0000 | 0.1000 | 0.5000 | 0.50 |
| 3 | 97.9000 | 1.0000 | 0.1000 | 1.0000 | 1.00 |
| 4 | 97.4000 | 1.0000 | 0.1000 | 1.5000 | 1.50 |
| 5 | 96.9000 | 1.0000 | 0.1000 | 2.0000 | 2.00 |
| 6 | 96.4000 | 1.0000 | 0.1000 | 2.5000 | 2.50 |
| 7 | 95.9000 | 1.0000 | 0.1000 | 3.0000 | 3.00 |
| 8 | 95.4000 | 1.0000 | 0.1000 | 3.5000 | 3.50 |
| 9 | 94.9000 | 1.0000 | 0.1000 | 4.0000 | 4.00 |
| 10 | 94.4000 | 1.0000 | 0.1000 | 4.5000 | 4.50 |
| 11 | 93.9000 | 1.0000 | 0.1000 | 5.0000 | 5.00 |
| 12 | 93.4000 | 1.0000 | 0.1000 | 5.5000 | 5.50 |
| 13 | 92.9000 | 1.0000 | 0.1000 | 6.0000 | 6.00 |
| 14 | 92.4000 | 1.0000 | 0.1000 | 6.5000 | 6.50 |
| 15 | 91.9000 | 1.0000 | 0.1000 | 7.0000 | 7.00 |
| 16 | 91.4000 | 1.0000 | 0.1000 | 7.5000 | 7.50 |
| 17 | 90.9000 | 1.0000 | 0.1000 | 8.0000 | 8.00 |
| 18 | 90.4000 | 1.0000 | 0.1000 | 8.5000 | 8.50 |
| 19 | 89.9000 | 1.0000 | 0.1000 | 9.0000 | 9.00 |
| 20 | 89.4000 | 1.0000 | 0.1000 | 9.5000 | 9.50 |
| 21 | 88.9000 | 1.0000 | 0.1000 | 10.0000 | 10.00 |

Figure 2:
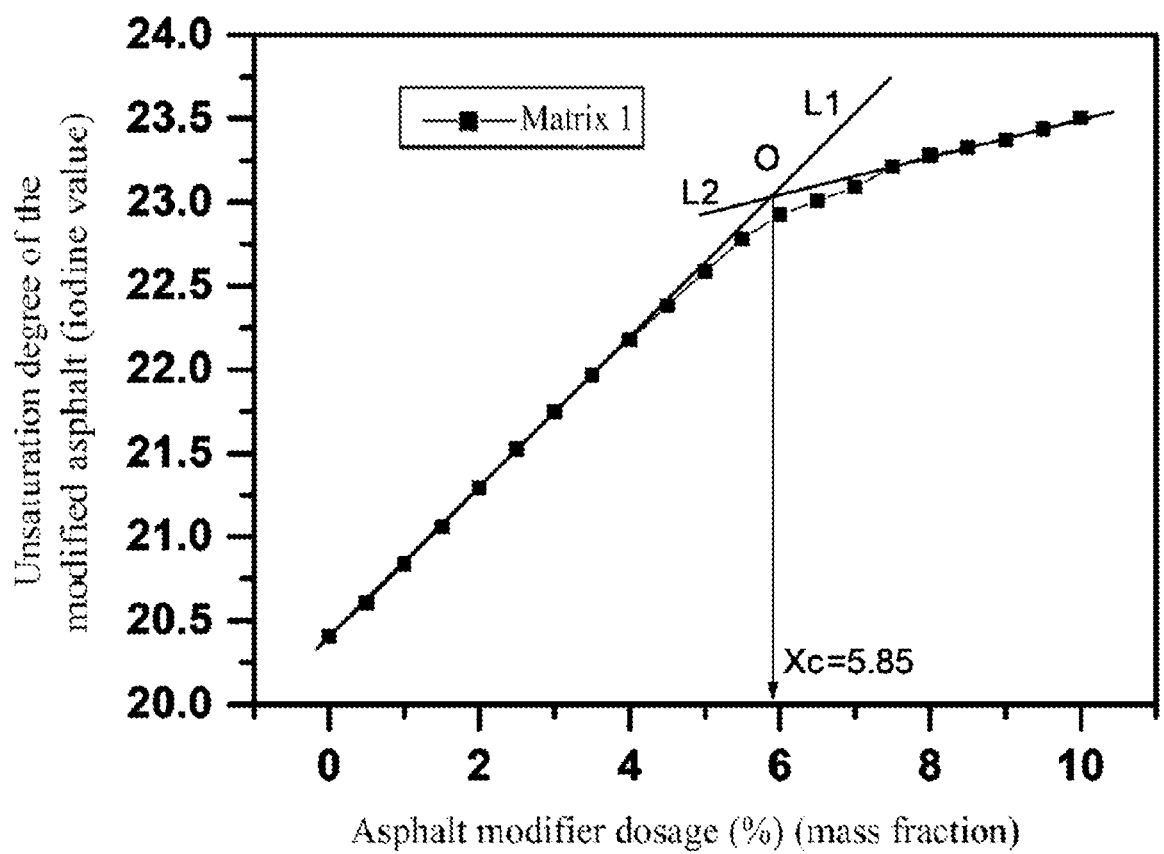
FIG. 2 is a diagram showing a curve of the unsaturation degree as a function of the modifier dosage, and partitioned linear fitting results in Example 1 of the present disclosure.

A design reference value quantification method for a modifier dosage of modified asphalt provided by the present disclosure was adopted, which was specifically conduced as follows:

step 1, a plurality of groups of tetrahydrofuran solutions of modified asphalt samples with different modifier dosages were prepared, where the mass of the modified asphalt sample in each group was 2.0 g, and the amount of tetrahydrofuran added was 50 mL;

step 2, 15 mL of a 0.1 M Wijs reagent was added to each tetrahydrofuran solution of the modified asphalt sample, and reacted at 45° C. for 8 h; 10 mL of a 10 g/L potassium iodide solution was added, and reacted for 5 min, obtaining product solutions;

step 3, each product solution obtained in step 2 was titrated with a 0.2 M sodium thiosulfate solution, a titration end point was determined by potentiometric titration, and a volume $V_1$ of the sodium thiosulfate consumed was determined, in mL, as shown in Table 2;

step 4, 50 mL of a blank tetrahydrofuran solution was prepared, and steps 2 and 3 were repeated to obtain a volume $V_0$ of the sodium thiosulfate solution consumed by the titration of the blank tetrahydrofuran solution, which was 24.4350 mL;

step 5, an unsaturation degree Y of each modified asphalt sample was calculated according to the formula (1), as shown in Table 2;

$$Y = \frac{126.9(V_0 - V_1)C}{10W} \quad (1)$$

where C refers to the concentration of sodium thiosulfate, 0.2 mol/L; and W refers to the mass of the modified asphalt sample, 2.0 g;

step 6, a curve was plotted with the modifier dosage as an abscissa and the unsaturation degree of the modified asphalt sample as an ordinate, as shown in FIG. 2; a straight line $L_1$ was fitted in a low-dosage region (ranging from 0 to 4.5%) of the modifier where the unsaturation degree showed linear growth, and a straight line $L_2$ was fitted in a high-dosage region (ranging from 7.5 to 10%) of the modifier where the unsaturation degree is in plateau; and step 7, an intersection point of the straight lines $L_1$ and $L_2$ was determined as the inflection point O of the unsaturation degree as a function of the modifier dosage, where an abscissa value corresponding to the inflection point O was 5.85%, i.e., a design reference value of the modifier dosage in the modified asphalt.

TABLE 2

Results of SBS-modified matrix asphalt-unsaturation degree determined by potentiometric titration

| SBS dosage/% | Titration volume ($V_1$)/mL | Unsaturation degree Y (A) |
|---|---|---|
| 0.0 | 8.4011 | 20.3470 |
| 0.5 | 8.1956 | 20.6078 |
| 1.0 | 8.0154 | 20.8365 |
| 1.5 | 7.8395 | 21.0597 |
| 2.0 | 7.6563 | 21.2922 |
| 2.5 | 7.4713 | 21.5269 |
| 3.0 | 7.2982 | 21.7466 |
| 3.5 | 7.1251 | 21.9663 |
| 4.0 | 6.9575 | 22.1789 |
| 4.5 | 6.7975 | 22.3820 |
| 5.0 | 6.6363 | 22.5866 |
| 5.5 | 6.4727 | 22.7942 |
| 6.0 | 6.4068 | 22.8778 |
| 6.5 | 6.3418 | 22.9603 |
| 7.0 | 6.2388 | 23.0910 |
| 7.5 | 6.1426 | 23.2131 |
| 8.0 | 6.0869 | 23.2837 |
| 8.5 | 6.0515 | 23.3287 |
| 9.0 | 6.0170 | 23.3724 |
| 9.5 | 5.9631 | 23.4408 |
| 10.0 | 5.9131 | 23.5043 |

Example 2

90# Matrix asphalt 2 provided by a well-known enterprise was used. According to the preparation process in the present disclosure, a certain amount of matrix asphalt and 1 g of furfural extract oil were weighed and heated to 175-180° C. SBS modifier was then added at a shear rate of 500 r/min at 175-180° C., and the resulting mixture was sheared at a shear rate of 3,000 r/min for 30 min to obtain a sample. The sample was transferred to a stirrer, and stirred at 500 r/min for 4 h, and then 0.1 g of sulfur powder as a stabilizer was added and stirred for 3 h for modification to obtain a modified asphalt. The method for preparing the modified asphalt was conducted by changing a single variable, i.e. all the modified asphalt samples were prepared with only difference in SBS modifier dosage. The formulation thereof is shown in Table 3.

TABLE 3

The formulation of the modified asphalt in Example 2

| No. | SK90# asphalt (g) | Furfural extract oil (g) | Sulfur powder (g) | SBS modifier (g) | SBS dosage (%) |
|---|---|---|---|---|---|
| 1 | 98.9000 | 1.0000 | 0.1000 | 0 | 0 |
| 2 | 98.4000 | 1.0000 | 0.1000 | 0.5000 | 0.50 |
| 3 | 97.9000 | 1.0000 | 0.1000 | 1.0000 | 1.00 |
| 4 | 97.4000 | 1.0000 | 0.1000 | 1.5000 | 1.50 |
| 5 | 96.9000 | 1.0000 | 0.1000 | 2.0000 | 2.00 |
| 6 | 96.4000 | 1.0000 | 0.1000 | 2.5000 | 2.50 |
| 7 | 95.9000 | 1.0000 | 0.1000 | 3.0000 | 3.00 |
| 8 | 95.4000 | 1.0000 | 0.1000 | 3.5000 | 3.50 |
| 9 | 94.9000 | 1.0000 | 0.1000 | 4.0000 | 4.00 |
| 10 | 94.4000 | 1.0000 | 0.1000 | 4.5000 | 4.50 |
| 11 | 93.9000 | 1.0000 | 0.1000 | 5.0000 | 5.00 |
| 12 | 93.4000 | 1.0000 | 0.1000 | 5.5000 | 5.50 |
| 13 | 92.9000 | 1.0000 | 0.1000 | 6.0000 | 6.00 |
| 14 | 92.4000 | 1.0000 | 0.1000 | 6.5000 | 6.50 |
| 15 | 91.9000 | 1.0000 | 0.1000 | 7.0000 | 7.00 |
| 16 | 91.4000 | 1.0000 | 0.1000 | 7.5000 | 7.50 |
| 17 | 90.9000 | 1.0000 | 0.1000 | 8.0000 | 8.00 |
| 18 | 90.4000 | 1.0000 | 0.1000 | 8.5000 | 8.50 |
| 19 | 89.9000 | 1.0000 | 0.1000 | 9.0000 | 9.00 |
| 20 | 89.4000 | 1.0000 | 0.1000 | 9.5000 | 9.50 |
| 21 | 88.9000 | 1.0000 | 0.1000 | 10.0000 | 10.00 |
| 22 | 88.4000 | 1.0000 | 0.1000 | 10.5000 | 10.5 |
| 23 | 87.9000 | 1.0000 | 0.1000 | 11.0000 | 11.00 |
| 24 | 87.4000 | 1.0000 | 0.1000 | 11.5000 | 11.50 |
| 25 | 86.9000 | 1.0000 | 0.1000 | 12.0000 | 12.00 |

Figure 3:
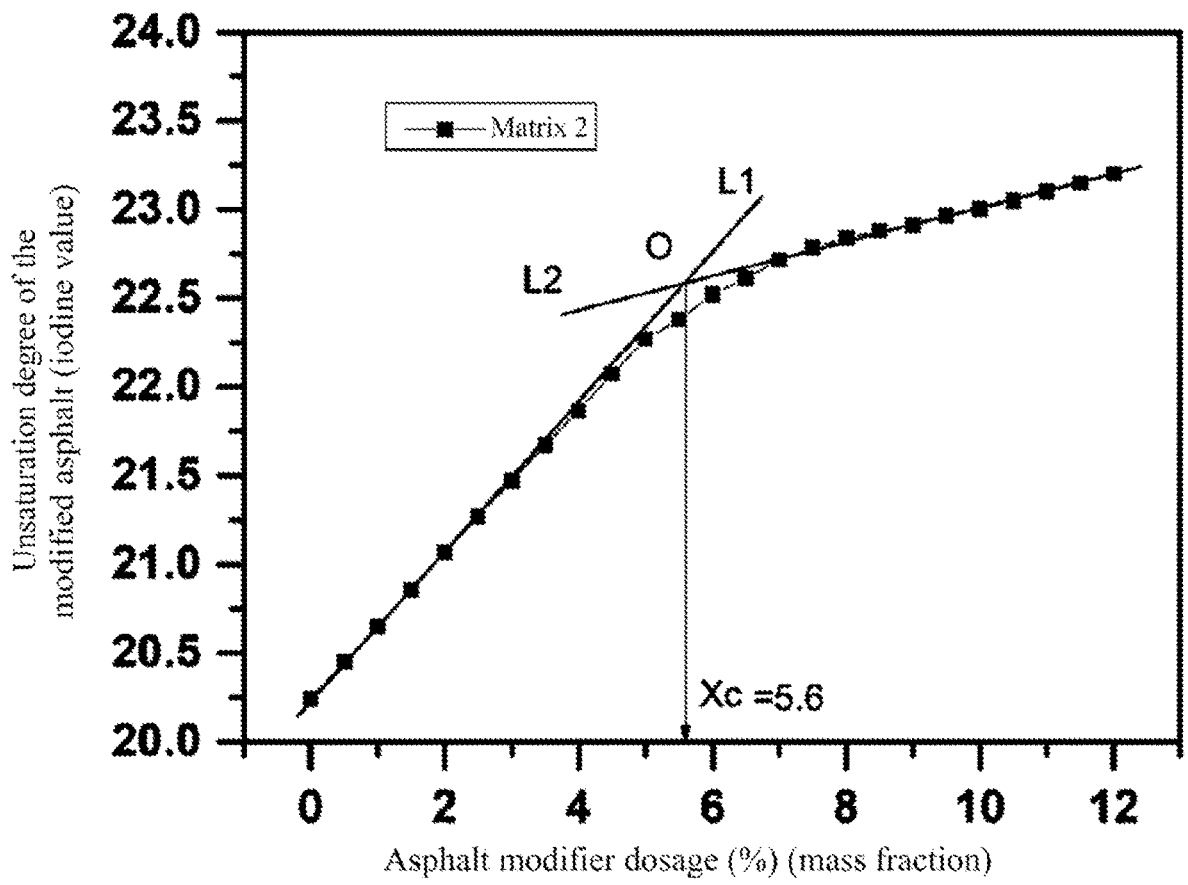
FIG. 3 is a diagram showing a curve of the unsaturation degree as a function of the modifier dosage, and partitioned linear fitting results in Example 2 of the present disclosure.

A design reference value quantification method for a modifier dosage of modified asphalt provided by the present disclosure was adopted, which was specifically conducted as follows:

step 1, a plurality of groups of tetrahydrofuran solutions of modified asphalt samples with different modifier dosages were prepared, where the mass of the modified asphalt sample in each group was 2.0 g, and the amount of tetrahydrofuran added was 55 mL;

step 2, 15 mL of a 0.2 M Wijs reagent was added to each tetrahydrofuran solution of the modified asphalt sample, and reacted at 35° C. for 12 h; 10 mL of a 10 g/L potassium iodide solution was added, and reacted for 3 min, obtaining product solutions;

step 3, each product solution obtained in step 2 was titrated with a 0.1998 M sodium thiosulfate solution, a titration end point was determined by potentiometric titration, and a volume $V_1$ of the sodium thiosulfate consumed was determined, in mL, as shown in Table 4;

step 4, 55 mL of a blank tetrahydrofuran solution was prepared, and steps 2 and 3 were repeated to obtain a volume $V_0$ of the sodium thiosulfate solution consumed by the titration of the blank tetrahydrofuran solution, which was 24.8350 mL;

step 5, an unsaturation degree Y of each modified asphalt sample was calculated according to the formula (1), as shown in Table 4;

$$Y = \frac{126.9(V_0 - V_1)C}{10W} \quad (1)$$

where C refers to the concentration of sodium thiosulfate, 0.1998 mol/L; and W refers to the mass of the modified asphalt sample, 2.0 g;

step 6, a curve was plotted with the modifier dosage as an abscissa and the unsaturation degree of the modified asphalt sample as an ordinate, as shown in FIG. 3; a straight line $L_1$ was fitted in a low-dosage region (ranging from 0 to 5%) of the modifier where the unsaturation degree showed linear growth, and a straight line $L_2$ was fitted in a high-dosage region (ranging from 7.5 to 12%) of the modifier where the unsaturation degree is in plateau; and step 7, an intersection point of the straight lines $L_1$ and $L_2$ was determined as the inflection point O of the unsaturation degree as a function of the modifier dosage, where an abscissa value corresponding to the inflection point O was 5.6%, i.e., a design reference value of the modifier dosage in the modified asphalt.

TABLE 4

Results of SBS-modified matrix asphalt-unsaturation degree determined by potentiometric titration

| SBS dosage/% | Titration volume ($V_1$)/mL | Unsaturation degree Y |
|---|---|---|
| 0 | 8.8692 | 20.2403 |
| 0.5 | 8.7037 | 20.4501 |
| 1 | 8.5449 | 20.6515 |
| 1.5 | 8.3823 | 20.8576 |
| 2 | 8.2163 | 21.068 |
| 2.5 | 8.0563 | 21.2709 |
| 3 | 7.8999 | 21.4691 |
| 3.5 | 7.7375 | 21.675 |
| 4 | 7.5886 | 21.8638 |
| 4.5 | 7.4268 | 22.0689 |
| 5 | 7.2660 | 22.2728 |
| 5.5 | 7.1823 | 22.3789 |
| 6 | 7.0703 | 22.5209 |
| 6.5 | 6.9991 | 22.6111 |
| 7 | 6.9172 | 22.7149 |
| 7.5 | 6.8610 | 22.7862 |
| 8 | 6.8186 | 22.8399 |
| 8.5 | 6.7861 | 22.8811 |
| 9 | 6.7611 | 22.9129 |
| 9.5 | 6.7211 | 22.9635 |
| 10 | 6.6913 | 23.0013 |
| 10.5 | 6.6536 | 23.0491 |
| 11 | 6.6128 | 23.1008 |
| 11.5 | 6.5773 | 23.1459 |
| 12 | 6.5353 | 23.1991 |

Example 3

70# Matrix asphalt 3 provided by a well-known enterprise was used. According to the preparation process in the present disclosure, a certain amount of matrix asphalt and 1 g of furfural extract oil were weighed and heated to 175-180° C. SBS modifier was then added at a shear rate of 500 r/min at 175-180° C., and the resulting mixture was sheared at a shear rate of 3,000 r/min for 30 min to obtain a sample. The sample was transferred to a stirrer, and stirred at 500 r/min for 4 h, and then 0.1 g of sulfur powder as a stabilizer was added and stirred for 3 h for modification to obtain a modified asphalt. The method for preparing the modified asphalt was conducted by changing a single variable, i.e. all the modified asphalt samples were prepared with only difference in SBS modifier dosage. The formulation thereof is shown in Table 5.

TABLE 5

The formulation of the modified asphalt in Example 3

| No. | SK70# asphalt (g) | Furfural extract oil (g) | Sulfur powder (g) | SBS modifier (g) | SBS dosage (%) |
|---|---|---|---|---|---|
| 1 | 98.9000 | 1.0000 | 0.1000 | 0 | 0 |
| 2 | 98.4000 | 1.0000 | 0.1000 | 0.5000 | 0.50 |
| 3 | 97.9000 | 1.0000 | 0.1000 | 1.0000 | 1.00 |
| 4 | 97.4000 | 1.0000 | 0.1000 | 1.5000 | 1.50 |
| 5 | 96.9000 | 1.0000 | 0.1000 | 2.0000 | 2.00 |
| 6 | 96.4000 | 1.0000 | 0.1000 | 2.5000 | 2.50 |
| 7 | 95.9000 | 1.0000 | 0.1000 | 3.0000 | 3.00 |
| 8 | 95.4000 | 1.0000 | 0.1000 | 3.5000 | 3.50 |
| 9 | 94.9000 | 1.0000 | 0.1000 | 4.0000 | 4.00 |
| 10 | 94.4000 | 1.0000 | 0.1000 | 4.5000 | 4.50 |
| 11 | 93.9000 | 1.0000 | 0.1000 | 5.0000 | 5.00 |
| 12 | 92.9000 | 1.0000 | 0.1000 | 6.0000 | 6.00 |
| 13 | 91.9000 | 1.0000 | 0.1000 | 7.0000 | 7.00 |
| 14 | 90.9000 | 1.0000 | 0.1000 | 8.0000 | 8.00 |
| 15 | 89.9000 | 1.0000 | 0.1000 | 9.0000 | 9.00 |
| 16 | 88.9000 | 1.0000 | 0.1000 | 10.000 | 10.00 |
| 17 | 87.9000 | 1.0000 | 0.1000 | 11.0000 | 11.00 |
| 18 | 86.9000 | 1.0000 | 0.1000 | 12.0000 | 12.00 |
| 19 | 85.9000 | 1.0000 | 0.1000 | 13.0000 | 13.00 |
| 20 | 84.9000 | 1.0000 | 0.1000 | 14.0000 | 14.00 |
| 21 | 83.9000 | 1.0000 | 0.1000 | 15.0000 | 15.00 |

Figure 4:
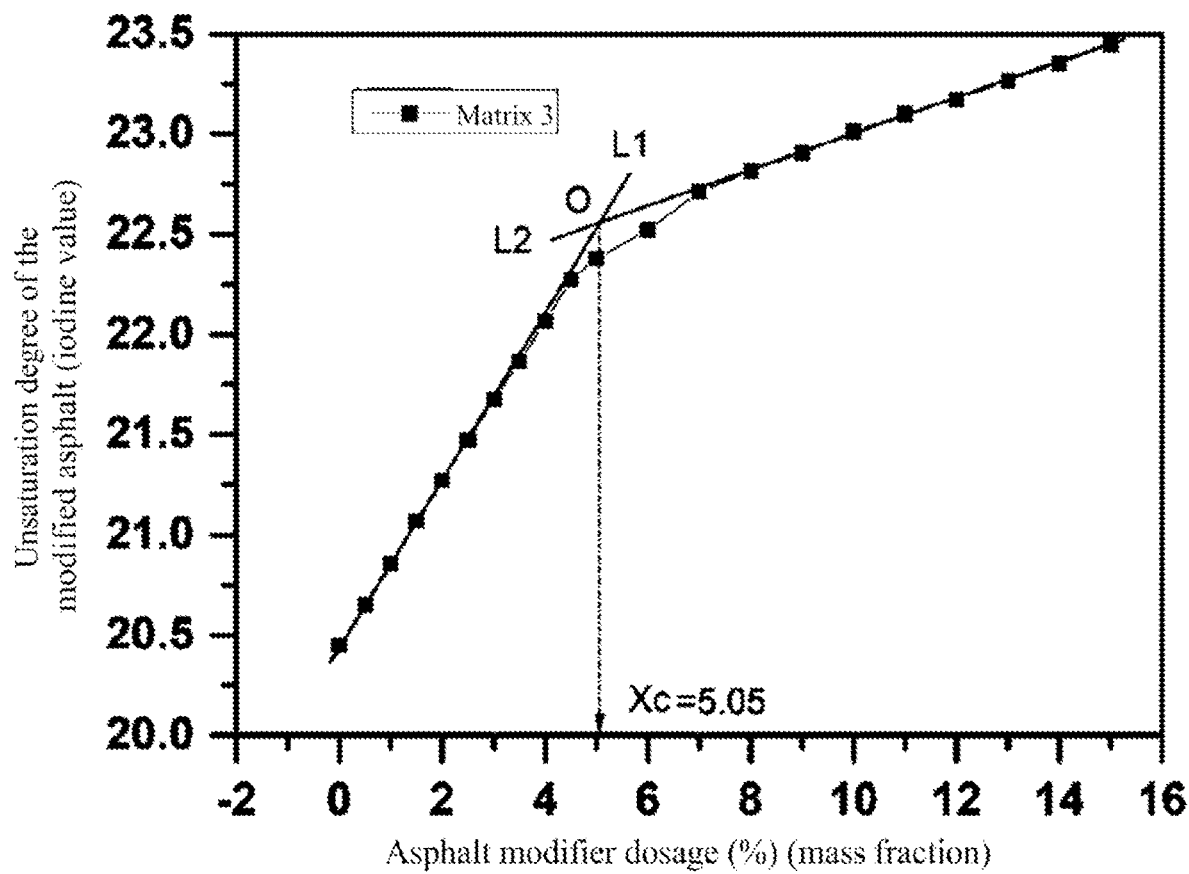
FIG. 4 is a diagram showing a curve of the unsaturation degree as a function of the modifier dosage, and partitioned linear fitting results in Example 3 of the present disclosure.

A design reference value quantification method for a modifier dosage of modified asphalt provided by the present disclosure was adopted, which was specifically conducted as follows:

step 1, a plurality of groups of tetrahydrofuran solutions of modified asphalt samples with different modifier dosages were prepared, where the mass of the modified asphalt sample in each group was 2.0 g, and the amount of tetrahydrofuran added was 50 mL;

step 2, 15 mL of a 0.1 M Wijs reagent was added to each tetrahydrofuran solution of the modified asphalt sample, and reacted at 50° C. for 4 h; 10 mL of a 10 g/L potassium iodide solution was added, and reacted for 8 min, obtaining product solutions;

step 3, each product solution obtained in step 2 was titrated with a 0.1978 M sodium thiosulfate solution, a titration end point was determined by potentiometric titration, and a volume $V_1$ of the sodium thiosulfate consumed was determined, in mL, as shown in Table 6;

step 4, 50 mL of a blank tetrahydrofuran solution was prepared, and steps 2 and 3 were repeated to obtain a volume $V_0$ of the sodium thiosulfate solution consumed by the titration of the blank tetrahydrofuran solution, which was 24.6350 mL;

step 5, an unsaturation degree Y of each modified asphalt sample was calculated according to the formula (1), as shown in Table 6;

$$Y = \frac{126.9(V_0 - V_1)C}{10W} \qquad (1)$$

where C refers to the concentration of sodium thiosulfate, 0.1978 mol/L; and W refers to the mass of the modified asphalt sample, 2.0 g;

step 6, a curve was plotted with the modifier dosage as an abscissa and the unsaturation degree of the modified asphalt sample as an ordinate, as shown in FIG. 4; a straight line $L_1$ was fitted in a low-dosage region (ranging from 0 to 4.5%) of the modifier where the unsaturation degree showed linear growth, and a straight line $L_2$ was fitted in a high-dosage region (ranging from 8 to 15%) of the modifier where the unsaturation degree is in plateau; and step 7, an intersection point of the straight lines $L_1$ and $L_2$ was determined as the inflection point O of the unsaturation degree as a function of the modifier dosage, where an abscissa value corresponding to the inflection point O was 5.05%, i.e., a design reference value of the modifier dosage in the modified asphalt.

TABLE 6

Results of SBS-modified matrix asphalt-unsaturation degree determined by potentiometric titration

| SBS dosage/% | Titration volume ($V_1$)/mL | Unsaturation degree Y |
|---|---|---|
| 0 | 8.3408 | 20.4499 |
| 0.5 | 8.1801 | 20.6516 |
| 1 | 8.0160 | 20.8575 |
| 1.5 | 7.8484 | 21.0679 |
| 2 | 7.6868 | 21.2707 |
| 2.5 | 7.5289 | 21.4689 |
| 3 | 7.3647 | 21.6749 |
| 3.5 | 7.2141 | 21.8639 |
| 4 | 7.0504 | 22.0694 |
| 4.5 | 6.8886 | 22.2725 |
| 5 | 6.8040 | 22.3786 |
| 6 | 6.6905 | 22.5211 |
| 7 | 6.5391 | 22.7111 |
| 8 | 6.4564 | 22.8149 |
| 9 | 6.3836 | 22.9062 |
| 10 | 6.3010 | 23.0099 |
| 11 | 6.2301 | 23.0989 |
| 12 | 6.1711 | 23.1729 |
| 13 | 6.0990 | 23.2635 |
| 14 | 6.0290 | 23.3513 |
| 15 | 5.9511 | 23.4491 |

The above merely describes preferred examples of the present disclosure, and the protection scope of the present disclosure is not limited to the above examples. Improvements and modifications obtained by those skilled in the art without departing from the technical concept of the present disclosure should be regarded as falling within the protection scope of the present disclosure.

What is claimed is:

1. A design reference value quantification method for a modifier dosage of modified asphalt, comprising the steps of:
    (1) preparing a series of modified asphalt samples with different modifier dosages;
    (2) determining an unsaturation degree of each modified asphalt sample by potentiometric titration;
    (3) obtaining an inflection point of the unsaturation degree of the modified asphalt sample as a function of the modifier dosage by data fitting; and
    (4) determining a reference value of the modifier dosage by the inflection point;
    wherein step (1) is conducted as follows:
    preparing a plurality of groups of tetrahydrofuran solutions of modified asphalt samples with different modifier dosages, wherein each group comprises the modified asphalt sample in an amount of 0.5-10 g, and the tetrahydrofuran in an amount of 55-100 mL; and
    step (2) is conducted as follows:
    S1, adding 10-30 mL of a 0.01-1 M Wijs reagent to each tetrahydrofuran solution of the modified asphalt sample, and reacting at 30-50° C. for 8-24 h; adding 5-30 mL of a 10-1,000 g/L potassium iodide solution, and reacting for 1-60 min, to obtain product solutions;
    S2, titrating each product solution obtained in step S1 with a 0.1-2 M sodium thiosulfate solution, determining a titration end point by potentiometric titration, and recording a volume $V_1$ of the sodium thiosulfate solution consumed, in mL;
    S3, preparing a blank tetrahydrofuran solution, and repeating steps S1 and S2 to obtain a volume $V_0$ of the sodium thiosulfate solution consumed by the titration of the blank tetrahydrofuran solution, in mL; and
    S4, calculating the unsaturation degree Y of the modified asphalt sample according to formula (1);

$$Y = \frac{126.9(V_0 - V_1)C}{10W} \quad (1)$$

wherein C refers to the concentration of sodium thiosulfate, in mol/L; 126.9 refers to the molar mass of iodine molecule, in g/mol; and W refers to the mass of the modified asphalt sample, in g.

2. The design reference value quantification method for a modifier dosage of modified asphalt of claim 1, wherein the modifier dosage in the modified asphalt sample is 0-20 wt %, and the modifier dosage changes in a linear gradient.

3. The design reference value quantification method for a modifier dosage of modified asphalt of claim 1, wherein the modifier is a polymer material containing olefinic bonds and acetylenic bond.

4. The design reference value quantification method for a modifier dosage of modified asphalt of claim 3, wherein the modifier is one or more selected from the group consisting of styrene-butadiene-styrene, styrene-butadiene rubber, and polyisoprene rubber.

5. The design reference value quantification method for a modifier dosage of modified asphalt of claim 1, wherein step (3) is conducted as follows:
    a) plotting a curve with the modifier dosage as an abscissa and the unsaturation degree of the modified asphalt sample as an ordinate;
    b) fitting a straight line $L_1$ in a low-dosage region (ranging from 0 to 10%) of the modifier where the unsaturation degree shows linear growth, and fitting a straight line $L_2$ in a high-dosage region (ranging from 6 to 20%) of the modifier where the unsaturation degree is in plateau; and
    c) determining an intersection point of the straight lines $L_1$ and $L_2$ as the inflection point O of the unsaturation degree as a function of the modifier dosage.

6. The design reference value quantification method for a modifier dosage of modified asphalt of claim 1, wherein in step (4), the abscissa value corresponding to the inflection point O indicates a design reference value of the modifier dosage in the modified asphalt.

* * * * *